(12) United States Patent
Tanny et al.

(10) Patent No.: US 6,527,146 B1
(45) Date of Patent: Mar. 4, 2003

(54) WATER DISPENSING APPARATUS WITH FILTER INTEGRITY TESTING SYSTEM

(75) Inventors: Gerald Tanny, Rehovot (IL); Peter Hulley, Port St. Mary (GB); Michael Anthony Thomson, Maxey (GB)

(73) Assignee: Soda-Club (CO2) Atlantic GmbH, Zug (CH)

( * ) Notice: Subject to any disclaimer, the term of this patent is extended or adjusted under 35 U.S.C. 154(b) by 0 days.

(21) Appl. No.: 09/937,269

(22) PCT Filed: Apr. 3, 2000

(86) PCT No.: PCT/IL00/00207
§ 371 (c)(1),
(2), (4) Date: Nov. 27, 2001

(87) PCT Pub. No.: WO00/59615
PCT Pub. Date: Oct. 12, 2000

(30) Foreign Application Priority Data

Apr. 4, 1999 (IL) .................................................. 129308

(51) Int. Cl.⁷ ............................................. B01D 35/00
(52) U.S. Cl. ............................ 222/189.11; 222/189.06
(58) Field of Search ....................... 222/189.06, 189.11

(56) References Cited

U.S. PATENT DOCUMENTS

| 4,369,898 A | * | 1/1983 | Andersson ..................... 222/4 |
| 4,515,007 A | | 5/1985 | Herman |
| 4,528,093 A | * | 7/1985 | Winer ....................... 210/96.2 |

(List continued on next page.)

FOREIGN PATENT DOCUMENTS

| DE | 43 39 589 C1 | 12/1994 |
| EP | 0 335 647 | 10/1989 |
| EP | 0 585 822 B1 | 2/1994 |
| HU | 400 U | 6/1993 |
| HU | 1487 U | 1/1998 |
| HU | 1542 U | 7/1998 |
| HU | 1731 U | 4/2001 |

OTHER PUBLICATIONS

Patent Abstracts of Japan, Publication No. 62–140607, "Method for Sterilely Detecting Leak of Hollow YarnType Module". Jun. 24, 1987.

Patent Abstracts of Japan, Publication No. 09–075690, "Method and Device for Detecting Damage of Water Treatment Filter and Water Treatment Apparatus Equipped with the Same". Mar. 25, 1997.

Patent Abstracts of Japan, Application No. 05303302. "Integrity Test Method for Virus Removing Membrane". May 23, 1995.

Predicting Log Removal Performance of Membrane Systems using In–Situ Integrity Testing. *Filtration & Separation*, Jan./Feb. 1998, pp. 26–29.

*Primary Examiner*—J. Casimer Jacyna
(74) *Attorney, Agent, or Firm*—Merchant & Gould P.C.

(57) ABSTRACT

Water dispenser, which comprises, in addition to a water container, a filter element contained within a filter housing having an inlet and a dispensing outlet, a source of pressure and first valve and first conduit means for feeding water from the container to the filter housing inlet; means for feeding gas to the filter inlet to create gas pressure at the inlet, consisting of a reservoir, and the control means comprise the third conduit and valve means for permitting or preventing the admission of water into the reservoir, second valve and conduit means for controlling the level of the water in the reservoir, a pressure gauge for monitoring the pressure at the filter inlet; and control means for controlling the gas feeding means to cause or stop the feeding. The source of pressure may be a compressed gas cylinder provided with valve and conduit means for controlling the admission of compressed gas from the cylinder into the water container, and the means for feeding gas to the filter inlet comprise conduit and valve means for feeding gas to the inlet directly from the gas cylinder.

30 Claims, 3 Drawing Sheets

U.S. PATENT DOCUMENTS

| | | |
|---|---|---|
| 4,744,240 A | 5/1988 | Reichelt |
| 4,779,448 A | 10/1988 | Gogins |
| 4,872,974 A | 10/1989 | Hirayama et al. |
| 4,969,991 A * | 11/1990 | Valadez .................... 210/96.2 |
| 5,064,529 A | 11/1991 | Hirayama et al. |
| 5,282,380 A | 2/1994 | Dileo et al. |
| 5,353,630 A | 10/1994 | Soda et al. |
| 5,417,101 A | 5/1995 | Weich |
| 5,477,896 A * | 12/1995 | Grifols Lucas .............. 141/83 |
| 5,480,554 A | 1/1996 | Degen et al. |
| 5,484,538 A * | 1/1996 | Woodward .................. 210/767 |
| 5,507,959 A | 4/1996 | Glick |
| 5,594,161 A | 1/1997 | Randhahn et al. |
| 5,607,593 A | 3/1997 | Cote et al. |
| 5,676,824 A * | 10/1997 | Jeon et al. .................... 210/85 |
| 5,685,991 A | 11/1997 | Degen et al. |
| 5,788,862 A | 8/1998 | Degen et al. |
| 5,808,181 A | 9/1998 | Wamsiedler et al. |
| 5,817,231 A * | 10/1998 | Souza ...................... 210/96.2 |

* cited by examiner

WATER DISPENSING APPARATUS WITH FILTER INTEGRITY TESTING SYSTEM

FIELD OF THE INVENTION

The present invention relates to a water dispensing apparatus, which provides filtered water free of specific microorganisms, and comprises means for assuring the filter integrity. The dispensing apparatus of this invention is particularly intended for drinking water in domestic use.

BACKGROUND OF THE INVENTION

Various types of domestic drinking water purification systems, which claim to provide microorganism-free filtered water, are known in the art The most commonly used systems remove protozoan cysts, such as *cryptorsproridium Parvum* and *giaria Lablia*, which may be found in insufficiently chlorinated water supplies. As the cysts are from 5–10 microns in size, they are typically removed by a one micron rated microporous filter element, usually fabricated from carbon block, so that it simultaneously removes chlorine and other impurities to improve taste. Submicron microporous filters fabricated from ceramic or synthetic polymeric materials, with a maximum pore size of 0.2 micron, are also known. Such filters are capable of removing pathogenic bacteria such as *pseudomonas Aurigena*, which may also be found in domestic, treated water supplies. The danger is that the users of such filters may be given a false sense of security at times when such organisms are discovered in the local water supply and a "boil water" alert is issued by the authorities. Although several such filters may be performance-tested when certified for the validity of their claims, few, if any, claim to 100% quality assure every filter unit sold Thus, some finite fraction of units sold do not in fact meet the claimed retention In addition, the filter element might either have been damaged prior to being installed, or might be improperly installed by the user in the housing, such that leakage of unfiltered water into the final product is possible. Finally, glue seals to the filter in the fabricated filter element can sometimes fail over time in an aqueous environment, depending on factors such as pH and temperature and the number of mechanical shocks given to the system during opening and closing the water supply to the system. In all of the above instances, since such purification systems do not comprise means for testing the integrity of the filter, the user has no way to verify if the system will in fact perform according to claimed performance specifications.

Means for testing filter integrity are also known in the art. Thus, U.S. Pat. No. 4,872,974 discloses a membrane filter testing method, which comprises increasing the pressure at the primary side of a membrane filter fixedly accommodating the housing and wetted with a liquid, by a gas at a predetermined rate, and checking whether the pressure at the primary side of the membrane filter is within a specified judging range after the lapse of a predetermined period of time.

U.S. Pat. No. 5,417,101 discloses a method and apparatus for isolating defective filter elements by measuring a gas flow rate under known pressure conditions through said elements.

U.S. Pat. No. 5,594,161 discloses a method of testing the integrity of a filter element in a filter assembly which includes wetting the filter, subjecting the inlet side of the filter to a gas pressure, measuring the pressure in the outlet conduit as a function of time, and determining whether a pressure measurement at a preselected time exceeds a reference pressure by a predetermined amount.

An article entitled "Predicting . . . Removal Performance of membrane Systems using In Situ Integrity Testing", published in Filtration and Separation, January, February 1998, pp. 26–29, describes two main methods for testing membrane systems integrity, the first of which consists in applying air at a pressure bubble point to one side of the membrane, isolating and then measuring the declining pressure over time. The bubble point hereinbefore referred to, or more exactly, the bubble point pressure, is defined as the pressure required for forcing the air to flow through the pores of a membrane whose pores have been initially completely filled by a liquid. The other method consists in filling the shell of the module with a liquid and allowing the air leakage to displace liquid from the shell. The flow rate of displaced liquid is then a direct measure of the membrane integrity.

The testing methods of the prior art, as summarized hereinbefore, and in general, all the methods of the art, require the measurement of a physical quantity, be it a volume or a pressure, and therefore, a certain degree of expertise on the operator's part and the presence of the required measurement components. They are, therefore, unsuited to a domestic drinking water apparatus. On the other hand, domestic apparatus should be provided with methods for testing the integrity of the filter, to avoid the danger of a supply of unsafe water.

It is therefore a purpose of this invention to provide a domestic water-dispensing apparatus that is provided with the means for testing the integrity of the filter.

It is another purpose of the invention to provide a domestic water-dispensing method and apparatus that do not require the measurement of physical quantities, and judge the integrity of the filter by visual inspection or by sensing of a physical property for the presence of air bubbles.

It is a further purpose of this invention to provide such a method and apparatus that are simple and of simple and secure operation and require no expertise on the user's part.

It is a still further purpose of this invention to provide a domestic water-dispensing apparatus, comprising means for determining the filter integrity, which are simple in structure and operation and economical.

It is a still further purpose of this invention to provide a domestic water-dispensing apparatus, comprising automatically controlled means for determining the filter integrity.

Other purposes and advantages of the invention will appear as the description proceeds.

SUMMARY OF THE INVENTION

The water dispenser with filter tester according to this invention comprises:

1—a water container,
2—a filter contained within a pressurizable housing having an inlet and a dispensing outlet connected to the filtered fluid side of the filter;
3—a source of pressure;
4—first valve and conduit means for leading water from said container to the filter housing inlet; and further comprises:
5—means for feeding gas to said filter housing inlet to generate gas pressure at said inlet;
6—a pressure gauge or transducer for monitoring the pressure at the filter housing inlet; and 7—control means for controlling said gas feeding means to cause or stop said feeding.

In a form of the invention, the means for feeding gas to said filter housing inlet comprise:

a—a reservoir, b—second valve and conduit means for controlling the level of the water in said reservoir; and c—third conduit and valve means for connecting said reservoir to said filter housing at a second inlet;

and the control means for controlling the gas feeding to the filter housing inlet comprise third valve and conduit means to permit or prevent the admission of water into said reservoir.

In said first form of the invention, the source of pressure is preferably a pump or a cylinder containing compressed gas and provided with valve and conduit means for controlling the admission of compressed gas from said cylinder into said water container. If the source of pressure is a pump, said second valve and conduit means connect said reservoir to said pump and/or to said filter housing inlet or disconnect said reservoir from said pump and/or said filter housing inlet If the source of pressure is a compressed gas cylinder, said second valve and conduit means connect said reservoir to said water container when compressed gas has been admitted into it and/or to said filter housing inlet or disconnect said reservoir from said container and/or to said filter housing inlet.

In a second form of the invention, the source of pressure is a compressed gas cylinder provided with valve and conduit means for controlling the admission of compressed gas from said cylinder into said water container, and the means for feeding gas to said filter housing inlet comprise conduit and valve means for feeding gas to said filter directly from said gas cylinder.

In said first form of the invention, said second valve and conduit means, when open, selectively allow said source of pressure to feed water into said reservoir, whereby to displace air therefrom or to draw water therefrom, selectively to cause water partially to fill said reservoir to a predetermined, normal level or to a higher testing level.

Said third conduit and valve means, when open, permit to introduce into said second filter housing inlet air displaced by water fed into said reservoir and to displace air and/or water from the inlet side of said filter housing. Preferably, said filter housing is provided, in addition to said dispensing outlet, with a second outlet on the inlet side of the filter, which is more preferably a feedback outlet connected to conduit means for returning, to said water container, water displaced from said filter.

The control means are programmed, in the first form of the invention, so as to actuate the source of pressure when said second valve and conduit means connect it to said reservoir, and stop it when said pressure measurement means indicates that the air pressure at the filter housing inlet has reached a predetermined test pressure, which is lower than the bubble point pressure of the filter. The predetermined air pressure is chosen in relation to the pore size and function of the filter and the meaning of the test of integrity. If one defines gross mechanical failure as a defect of 10 microns or more, then the predetermined integrity test pressure is set at a value whose minimum is 0.2 bar , and whose maximum is a pressure equal to 80% of the bubble point pressure of the filter.

In said second form of the invention, the conduit and valve means for feeding gas to the filter directly from said gas cylinder are activated to stop said gas feeding when the pressure at the filter housing inlet has reached said predetermined test pressure, lower than the bubble point pressure.

If at the test pressure bubbles appear at the filter housing outlet, this means that filter integrity is lost. Then an alarm, with which the dispenser is provided, gives an acoustic or optical alarm signal, such as e.g. a warning light or a writing, to indicate that the integrity of the filter has been compromised and water from the outlet may not be of the specified purity which the filter is meant to deliver. The machine is then disactivated until the filter has been replaced. If no bubbles appear at the filter outlet, then the filter is normally fictional and the water is restored in the reservoir to a normal level, and the apparatus can be used, immediately or whenever required, as a filtered water dispenser.

It will be understood, therefore, that the water dispenser of the invention has three modes: the inactive mode, the dispensing mode, in which it operates as a conventional dispenser, and the testing mode, in which it permits a test of the integrity of the filter. In the inactive mode, all valves are closed. In the dispensing mode, the first valve and conduit means are open. In the test mode, gas is fed to the second filter housing inlet The control means are programmed to place the water dispenser in the dispensing or the testing mode, or to inactivate it, depending on a command which the dispenser user can give in any convenient, even conventional, way, e.g. by means of a key or keys connecting it to or disconnecting it from a power source, whether a power line or an independent source, such as battery, or selectively controlling circuits of a microprocessor, or the like. The dispenser is inactivated when it is efficient, but no water is to be dispensed, or when the filter is being replaced. After the test has been terminated and the filter has been replaced or it has been found that it should not be replaced, the apparatus is inactivated and is ready to be returned to the dispensing mode, or is directly returned to it It also follows logically from the above that the control means to the apparatus may be programmed to automatically carry out some combination of the three modes upon a single command by the user. Thus, after each dispense activation, or some preset number of dispense activations, the test may be automatically initiated.

While the invention is of particular interest for domestic water dispensers, this is not a limitation of the invention, since it is applicable to water dispensers in general, including industrial or public dispensers, regardless of their size or their specific use.

Correspondingly, the invention comprises a method for testing a filter contained within a pressurizable housing in a household water dispensing apparatus, which, in the first form of the invention, comprises the following steps:

1—providing a reservoir,

2—feeding water into it to a predetermined level; when it is desired to test the filter:

3—filling the filter housing with water and forcing water into all pores of the filter, 4—feeding water into said reservoir to raise the water level therein, while allowing air contained therein to flow out of said reservoir into the second filter housing inlet; thereby displacing the water contained in the inlet side of the filter housing through the second outlet, 5—monitoring the air pressure at the second filter housing inlet;

6—discontinuing the feeding of water into said reservoir when said pressure has become the test pressure; and 7—verifying whether air bubbles appear in the water issuing from a filter housing outlet, and if they do appear, substituting the filter, while if they do not appear, using the dispensing apparatus in the normal way.

It is obvious that the water is fed into the reservoir by means which depend on the source of pressure, and thus by pumping it if the source of pressure is a pump or by connecting the reservoir to the water container when this latter is under gas pressure, if the source of pressure is a compressed gas cylinder.

In the second form of the invention, after the housing and filter have been filled with water, the method comprises testing the filter by:

I—feeding gas to the housing inlet from the compressed gas cylinder;

II—monitoring the air pressure at the filter housing inlet;

III—discontinuing the feeding of gas when said pressure has become the test pressure; and IV—verifying whether air bubbles appear in the water issuing from a filter outlet, and if they do appear, substituting the filter, while if they do not appear, using the dispensing apparatus in the normal way.

Since raising the water to the higher level serves to create the predetermined test pressure by compressing the air above the water, different level ratios of the test level to that of the normal level may be adopted in individual cases, depending on the dimensions of the various parts of the apparatus, to achieve the correct pressure.

The filter be of any used in a water dispensing apparatus, particularly domestic ones, but may be, for example only, a microporous, 0.2 micron filter prepared from a synthetic polymer, such as polysulphone or nylon, or an inorganic polymer such as a ceramic material. Such filters have a bubble point pressure, when wetted with water, from 3.5 to 4.5 bar. Typically, such filters have intrinsic pure water flows of 20–40 cc/sq.cc. filter area/bar.

The volumes of the various parts of the apparatus depend on its use. By way of example, in a domestic dispenser, the water container may have a capacity from 0.5 to 5 liters, and the reservoir a volume from 50 cc to 1.5 liter.

The invention further comprises a method of operating a water dispenser, particularly a domestic one, having an inactive, a dispensing and a test mode, which comprises placing the dispenser in the test mode, carrying out the testing method hereinbefore described, substituting the filter if it is found to be faulty, and placing the dispenser back into the dispensing mode.

DETAILED DESCRIPTION OF PREFERRED EMBODIMENTS

Figure 1:
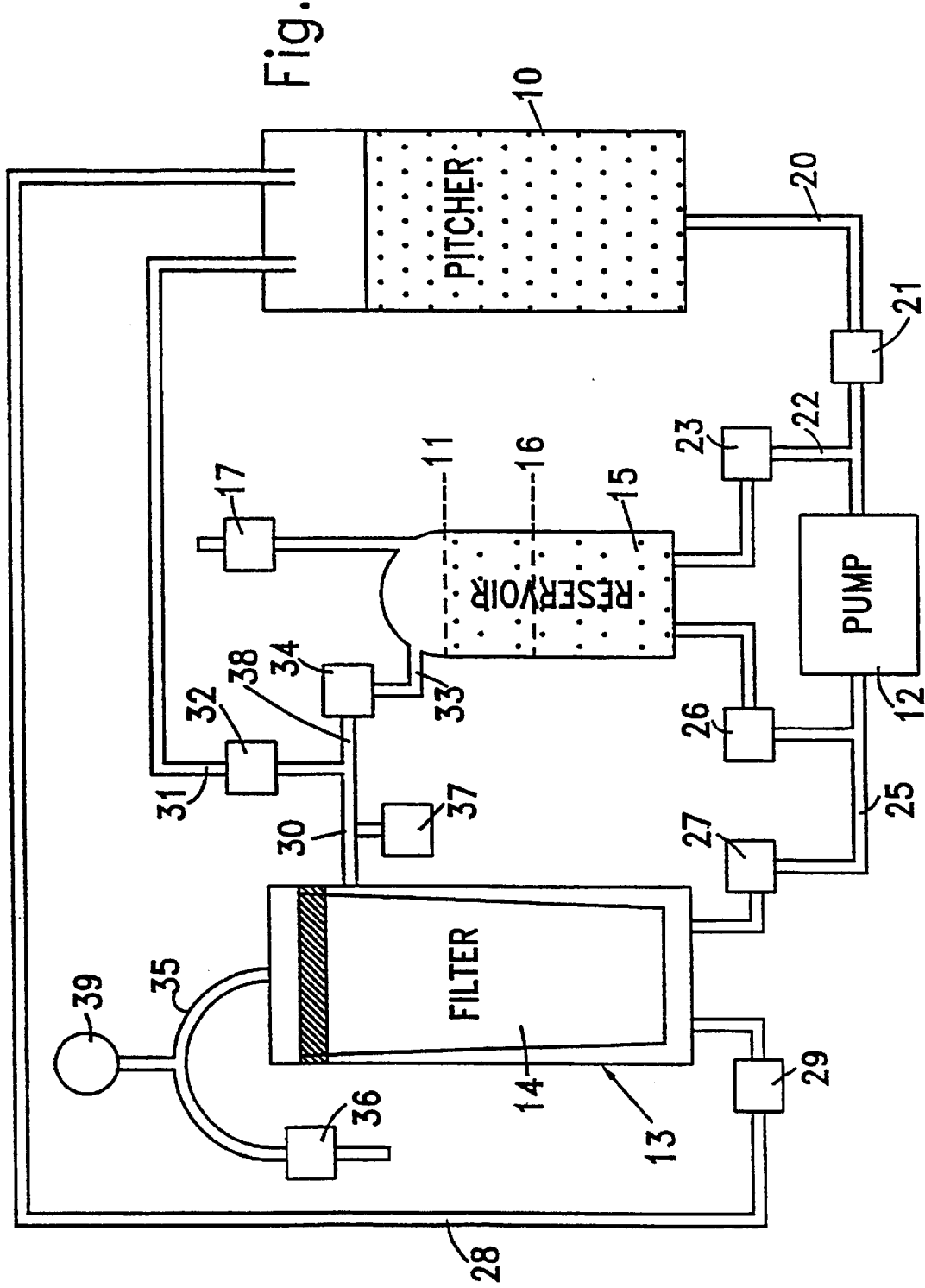
FIG. 1 is a schematic representation of an apparatus according to an embodiment of the invention.

Referring now to FIG. 1, numeral 10 designates the water container, which is filled by means not illustrated, and may be either manual or automatic in nature. Numeral 12 is a pump, and numeral 13 is the filter housing containing a filter 14. These are the normal components of a water-dispensing apparatus, and can be of any type known in the art other than what is specifically described herein. The filter is preferably chosen from among the group consisting of microporous synthetic membranes or microporous filters prepared from ceramic materials, metal, or carbon, with a nominal pore size of a value sufficient or smaller than that required to retain 99% or more of *cryptosporidium Parvum, giardia Lablia* and *pseudomonas Aurigena.*

Numeral 15 indicates a reservoir. In the normal dispensing operation, the water in reservoir 15 is at the level indicated by arrow 16, which will be called hereinafter the "normal level". Above that level, reservoir 15 is filled with air which can enter it through a valve 17, when this is open.

Water container 10 is connected to the inlet of pump 12 by conduit 20, which includes a valve 21. The inlet of pump 12 is also connected to reservoir 15 through pipe 22 and valve 23. The outlet of pump 12 is connected to a pipe 25, which has two branches, the first connected to valve 26 and through it to reservoir 15, and the second connected to valve 27 and through it to an opening into the inlet side of filter housing 13. Another such opening leads through a valve 29 into a conduit 28, which leads back to water container 10. Another opening on the inlet side of the filter housing is connected to a pipe 30, on which is mounted a pressure switch or transducer means 37, for confirming that the desired test pressure has been reached, and which branches out into branch 31, having a valve 32 and leading back to water container 10, and a branch 38, connected through valve 34 to reservoir 15. The filtered water outlet side of the filter housing is connected to a dispensing pipe 35 on which is mounted a one way dispensing check valve 36, which opens to dispense liquid upon the application of a small pressure (e.g. 0.05 bar) sufficient to overcome the force of the check valve. This valve seals the system against microbiological intrusion from the pure water side and also prevents dripping from the filter outlet when the dispense mode is not in operation. A bubble detector 39 is connected to pipe 35.

The operation of the machine, in its three modes, takes place according to the following stages.

Inactive mode:

1. When the machine is inactive, all valves are closed.

Dispensing mode:

2. To start the dispensing mode, a start signal is given in any appropriate way, e.g. by depressing a key which closes a circuit and connects the operative portions of the machine to a source of power.
3. Valve 21 opens, valve 27 opens, pump 12 starts, and water is pumped at a pressure sufficient t assure that it is transported from container 10 to the filter housing 13, through the filter 14 to dispensing valve 36, and, water is dispensed.

Test mode:

4. To stop the dispensing mode and prepare for the filter integrity check, a stop signal is given in any appropriate way, which resets all valves to the inactive, closed mode and closes pump 12.
5. Then valve 29 opens—to prevent further water being dispensed and reduces the pressure to atmospheric pressure in the filter.
6. Valves 26 and 21, and 34 open, and the pump is activated. This pumps water into reservoir 15 to allow the air in the reservoir to be pushed into the filter housing 13 and displace the water back to container 10 through exit pipe 28.
7. As soon as air is detected through the exit pipe 28, valve 29 closes, and air pressure builds in the filter housing 13 as more water enters reservoir 15.
8. The integrity check of the filter 14 starts now. The pressure at the filter inlet rises, until the test pressure, (e.g. 0.5 bar, which is preferably well below the filter's bubble point pressure) has been reached. At this point, the water in reservoir 15 will have reached the level indicated at 11, which is the highest level it is assumed to reach. Pressure switch or transducer means 34 will then confirm by appropriate signal that the test pressure has been reached and pump 12 will cease operation. If the filter 14 is integral, no air will pass 35, which is filled with water from the previous dispense cycle. If bubbles appear in it, bubble detector 39 will be activated and will generate an appropriate signal to indicate tat the filter is defective and must be replaced. At this point, the integrity check is finished, and valves 26 and 34 return to their closed state.

Return to inactive mode:

9. If the filter is found to be in satisfactory condition, or otherwise has been replaced, the machine must be readied for normal operation. For this purpose, an appropriate signal is given, valves 21 and 23 open to reduce pressure to atmospheric pressure and return water back to container 10 via valve 21. Air is now back in the top of the reservoir 15 and the level of water therein returns to the normal level.

10. Valve 21 closes, and valves 27, 17 and 32 open, pump 12 starts, and water is pumped from reservoir 15 into the filter housing 13 (timed such that it pumps all of the water and some additional air).

11. Valve 21 opens, valves 23 and 17 close, and water is pumped from container 10 to expel any additional air that may be in the filter housing 13 via valve 32 and pipe 31.

12. Pump 12 stops, and valves 21, 27 and 32 close. All valves are now closed and the machine is now inactive, but ready to be reactivated.

The water in tube 35 during the integrity test must be checked, as has been said, to determine whether bubbles are exiting from filter 14. The check could be a visual one, and such a check is included in the scope of the invention. However it is possible and preferred to effect the check by a device 39 that senses a physical parameter that is affected by the presence of bubbles, and generates a signal if bubbles are present. Said signal can produce a visual or acoustic alarm, or automatically set forth the procedure programmed for this case, which involves disactivating the machine and readying it for reactivation after the filter has been changed, as hereinbefore set forth in describing the operating cycle of the machine.

Figure 2:
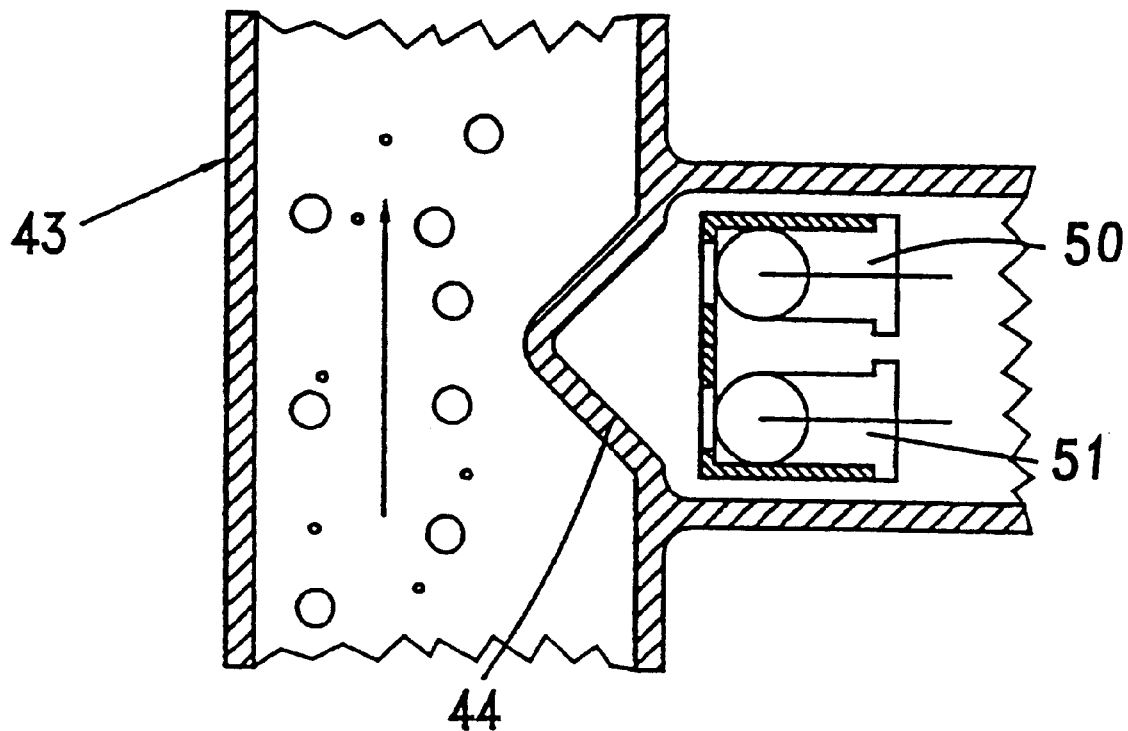
FIG. 2 schematically illustrates an embodiment of automatic bubble signaling device.

An example of optical-electronic, automatic bubble checking device is the following, illustrated in FIG. 2. It comprises an infrared transmitter/receiver pair (briefly, an "IR TD"), comprising an IR transmitter 50, an IR receiver 51, optical means, generally indicated at 42, for collecting the IR radiation from transmitter 50 and reflecting it back to receiver 51, an electronic alarm not shown, monitoring the intensity of the reflected radiation and so adjusted that it generates a signal if the intensity of the reflected IR radiation exceeds a predetermined threshold value. The water to be tested flows through a pipe 43, which is either transparent or has a transparent window 44, in front of said IR TD. If no bubbles are present, the reflected radiation sensed by IR sensor 41 has a certain value, which is taken as the threshold value. If bubbles pass in front of the IR TD, the increased reflection due to the bubbles causes the reflected radiation to exceed the threshold value, and the alarm means to react as programmed.

Figure 3:
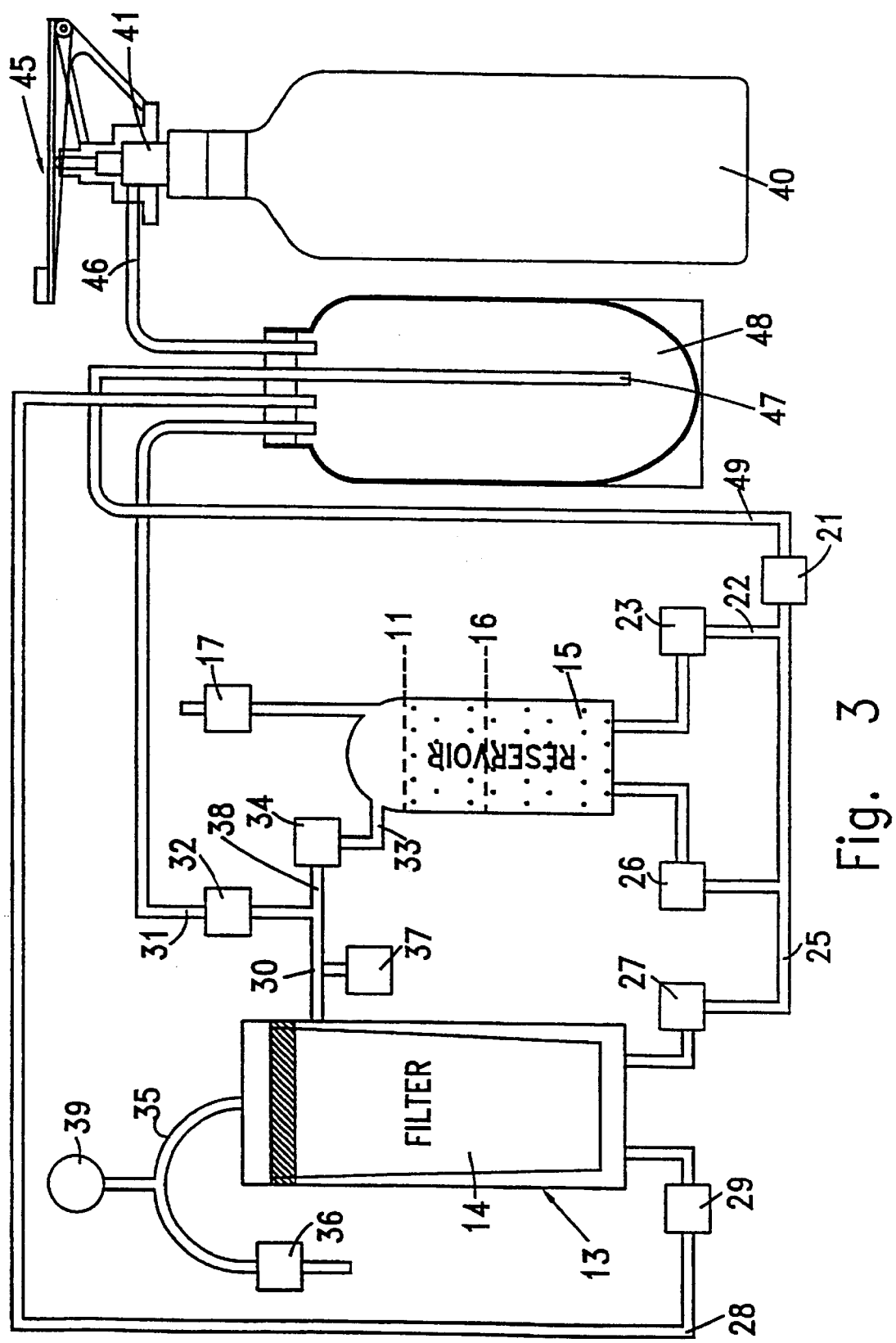
FIG. 3 is a schematic representation of an apparatus according to another embodiment of the invention.

As stated hereinbefore, the invention is not limited to the use of a pump, but any source of pressure can be used, in particular compressed gas, as e.g. in apparatus for carbonating beverages. Such an embodiment is illustrated, by way of example only, in FIG. 3. All the components of the embodiment of FIG. 3 that are or may be equal or equivalent to components of the embodiment of FIG. 1, are indicated by the same numerals. In this embodiment, a gas cylinder 40 is mounted on a cylinder holder generally indicated at 41. The cylinder holder may be of any kind adapted for liquid aerating machines and may be, in particular, such as described in EP 0 472 995 B1 or in PCT patent application IL 98/00470, and is therefore not described in detail. It will generally comprise means, such as screw means, for attaching the gas cylinder 40 to it, and a gas cylinder valve, unless this is part of the gas cylinder itself. As described in the aforesaid applications, the gas cylinder valve can be opened by any suitable means, such as a lever 45 to allow gas to escape from the gas cylinder. However, while the cylinder valve control means illustrated is a lever, that is normally hand-operated, this is merely a schematic illustration It is preferred that the apparatus be provided with control means, that will place it in the inactive, dispensing or test mode in response to a simple command given by the user, e.g. by depressing a key or the like; and therefore, when a compressed gas cylinder is used as a source of pressure, it is desirable to provide a cylinder valve that may be opened or closed by said control means, without direct manual intervention, and such valves are within the state of the art and need not be described or illustrated.

When the valve opening means is actuated and the cylinder valve is opened, the gas escapes through conduit 46. As described in the aforesaid PCT application, the inlet of said conduit may pass through a pre-filter, such as a small block of porous material fixed to the outlet of the cylinder holder and which retains unwanted particles that may block the subsequent gas passageways. Such a pre-filter will also perform as a safety feature, as it will reduce the risk of liquid carbon dioxide entering the main filter unit.

A water container 48, which has the same purpose as container 10 of FIG. 1, has an inlet in which opens gas conduit 46. It is further provided with a dip tube 47. Dip tube 47 is continued by conduit 49, leading to valve 21 and through it to conduit 25. Conduit 25 leads through valve 27 to filter housing 13 and branches out into two branches 22, both if which lead, through valves 23 and 26 respectively, to reservoir 15, as in the embodiment of FIG. 1. As in said embodiment, conduits 28 and 31 are feed-back conduits to water bottle 48.

The operation of this embodiment of the invention is the same as that of the first embodiment hereinbefore described, except that, instead of staring/stopping the pump to create or discontinue pressure, this is achieved by opening/closing the gas cylinder valve.

As has been said, in a second form of the invention the test of the filter can be carried out by feeding gas directly from a gas cylinder, such as cylinder 40, to the filter inlet. In that case, the reservoir 15, and conduits leading to and from it, can be omitted and conduit means can be provided leading directly from the gas cylinder to the filter inlet. Valve means will be provided selectively to connect the gas cylinder to the water container, when the apparatus is in the dispensing mode, or to the filter, when the apparatus is in the testing mode. Said valve means will be controlled, preferably by a program, to close and discontinue the gas feeding when the test pressure has been reached. In all other respects, the operation of the apparatus may be the same as described with reference to the first form of the invention.

It would also be possible, though less desirable, to provide the apparatus both with a pump and with a compressed gas cylinder, using the first to dispense water and the second to provide gas at test pressure to the filter, or to replace the water container by a direct connection to the water mains and provide gas for testing by a compressed gas cylinder.

Although embodiments of the invention have been described by way of illustration, it will be apparent that the invention can be carried out with many modifications, variations and adaptations, without departing from its spirit, or exceeding the scope of the claims.

What is claimed is:

1. Water dispenser, which comprises, in addition to a water container, a filter element contained within a filter housing having an inlet and a dispensing outlet, a source of pressure and first valve and first conduit means for feeding water from said container to said filter housing inlet:
   a—means for feeding gas to said filter housing inlet to create gas pressure at said inlet;
   b—a pressure gauge or other transduction means for monitoring the pressure at the filter inlet; and
   c—control means for controlling said gas feeding means to cause or stop said feeding.

2. Water dispenser according to claim 1, wherein the means for feeding gas to the filter inlet comprise:
   a—a reservoir;
   b—second valve and conduit means for controlling the level of the water in said reservoir; and
   c—the control means comprise third conduit and valve means for permitting or preventing the admission of water into said reservoir.

3. Water dispenser according to claim 2, wherein the source of pressure is a pump.

4. Water dispenser according to claim 3, wherein the second valve and conduit means connect the reservoir to the pump and/or to the filter housing inlet or disconnect said reservoir from said pump and/or said filter housing inlet.

5. Water dispenser according to claim 2, wherein the source of pressure is a container of compressed gas and conduit means for controlling the admission of compressed gas from said cylinder into the water container.

6. Water dispenser according to claim 5, wherein the second valve and conduit means connect the reservoir to the water container when compressed gas has been admitted into it and/or to the filter housing inlet or disconnect said reservoir from said container and/or said filter housing inlet.

7. Water dispenser according to claim 2, wherein the second valve and conduit means are such as to selectively allow the source of pressure to feed water into the reservoir, whereby to displace air therefrom or to draw water therefrom, selectively to cause water partially to fill said reservoir to a predetermined, normal level or to a higher testing level.

8. Water dispenser according to claim 2, wherein the third conduit and valve means are such as to permit to introduce, into the filter housing inlet, air displaced by water fed into the reservoir and to displace air and/or water from said filter housing.

9. Water dispenser according to claim 1, wherein the source of pressure is a compressed gas cylinder provided with valve and conduit means for controlling the admission of compressed gas from said cylinder into said water container, and the means for feeding gas to said filter inlet comprise conduit and valve means for feeding gas to said inlet directly from said gas cylinder.

10. Water dispenser according to claim 1, wherein the filter housing is provided, in addition to its dispensing outlet, with a second outlet on the filter inlet side.

11. Water dispenser according to claim 10, wherein the second outlet is a feedback outlet connected to conduit means for returning, to the water container, water displaced from the filter housing.

12. Water dispenser according to claim 1, wherein the control means for controlling the gas feeding means are activated to stop said feeding when the pressure at the filter inlet has reached a predetermined test pressure.

13. Water dispenser according to claim 12, wherein the test pressure is lower than the bubble point pressure of the filter element within the filter housing.

14. Water dispenser according to claim 12, further comprising an optical or acoustic alarm for signaling if, at the test pressure, bubbles appear at a filter outlet.

15. Water dispenser according to claim 1, wherein the control means comprise a microprocessor.

16. Water dispenser according to claim 1, wherein the control means are programmed selectively to place the dispenser in one of the following modes: inactive mode, in which the source of pressure is inactive and all the valve means are closed; dispensing mode, in which the source of pressure is activated and the first valve means are open; and test mode, in which gas is fed to the filter inlet.

17. Water dispenser according to claim 1, which is a domestic drinking water dispenser.

18. Water dispenser according to claim 17, wherein the source of pressure is chosen from the group consisting of pumps and containers of compressed gas.

19. Water dispenser according to claim 1, wherein the filter element is chosen from among the group consisting of microporous synthetic membranes, or microporous filters prepared from ceramic materials, metal, or carbon, with a nominal pore size of a value sufficient or smaller than that required to retain 99% or more of *cryptosporidium Parvum, giardia Lablia* and *pseudomonas Aurigena*.

20. Water dispenser according to claim 1, wherein the filter element has a bubble point pressure in the range of 0.5 bar to 8 bar.

21. Water dispenser according to claim 1, for domestic use, wherein the water container has a capacity from 0.5 to 5 liters.

22. Water dispenser according to claim 1, for domestic use, wherein the reservoir has a capacity from 50 cc to 1.5 liter.

23. Water dispenser according to claim 1, further comprising an electro-optical device for signaling the presence of air bubbles in a water stream issuing from a filter outlet, which comprises a radiation transmitter, a radiation receiver, a radiation transparent window for permitting the transmitted radiation to traverse the water stream, reflecting means for reflecting to said radiation receiver the radiation which has traversed the water stream, a radiation transparent window separating the water stream from said radiation transmitter and said radiation receiver, and electronic means for monitoring the intensity of the radiation received by said radiation receiver and generating a signal if said intensity exceeds a predetermined threshold.

24. Water dispenser according to claim 23, wherein the radiation is infrared radiation.

25. Method for testing the integrity of a filter element contained in a filter housing, in a household drinking water dispensing apparatus, which comprises the following steps:
   a—feeding gas to the filter inlet from a compressed gas cylinder;
   b—monitoring the gas pressure at the filter inlet;
   c—discontinuing the feeding of gas when said pressure has become the test pressure; and d—verifying whether air bubbles appear in the water issuing from a filter outlet, and if they do appear, substituting the filter, while if they do not appear, using the dispenser.

26. Method for testing the integrity of a filter element contained in a filter housing, in a household water dispensing apparatus, which comprises the following steps a—providing a reservoir;

b—feeding water into said reservoir to a predetermined, normal level;

when it is desired to test the filter:

c—filling all the pores of the filter element with water; by filtering water through the element in the normal operational mode;

d—feeding water into said reservoir to raise the water level therein to a test level, while allowing air contained therein to flow out of said reservoir into the filter housing inlet thereby displacing the water in the inlet side of the filter housing;

e—monitoring the air pressure at the filter inlet;

f—discontinuing the feeding of water into said reservoir when said inlet pressure has reached a predetermined test pressure sufficient to distinguish the existence of gross mechanical leaks either in the filter element, or allowing bypass to occur between the filter element and the filter housing; and g—verifying whether air bubbles appear in the water issuing from the filter housing outlet, and if they do appear, substituting the filter, while if they do not appear, using the dispensing apparatus in the normal way.

27. Method of operating a water dispenser having an inactive, a dispensing and an integrity test mode, which comprises placing the dispenser in the test mode, carrying out a testing method comprising creating at a filter housing inlet an air pressure lower than the bubble point pressure of the filter element contained within the filter housing, verifying whether air bubbles appear at the filter housing outlet, indicating a faulty filter, substituting the filter if it is found to be faulty, and placing the dispenser back into the inactive or dispensing mode.

28. Water dispenser, which comprises, in addition to a water container, a filter housing having an inlet and a dispensing outlet, a source of pressure and first valve and first valve and conduit means for feeding water from said container to said filter inlet:

a)—a reservoir;

b)—second valve and second conduit means connecting said reservoir to said source of pressure for selectively feeding water into said reservoir, whereby to displace air therefrom, or for drawing water therefrom, selectively to cause said reservoir to become partially filled to a normal level or to a testing level higher than said normal level;

c)—third valve and third conduit means for connecting said reservoir to said filter housing inlet, whereby to introduce into said filter housing inlet air displaced by water fed into said reservoir and to displace water from said filter housing to said outlet thereof;

d)—pressure measurement means for monitoring the pressure at the filter inlet; and e)—control means for causing said source of pressure and said second valve and conduit means to discontinue the feeding of water into said reservoir.

29. Water dispenser, which comprises, in addition to a water container, a filter element contained within a filter housing having an inlet and a dispensing outlet, a pump and first valve and first conduit means for pumping water from said container to said filter housing inlet:

a—a reservoir;

b—second valve and second conduit means for connecting said reservoir to said pump for controlling the level of the water in said reservoir;

c—third valve and third conduit means for connecting said reservoir to said filter housing inlet;

d—pressure measurement means for monitoring the pressure at the filter housing inlet; and e—control means for causing said second and third valve and conduit means to connect said reservoir to pump and/or to said filter housing inlet or disconnect said reservoir from said pump and/or said filter housing inlet.

30. Water dispenser, which comprises, in addition to a water container, a filter element contained within a filter housing having an inlet and a dispensing outlet, and first valve and first conduit means for feeding water from said container to said filter housing inlet:

a—a filter element contained within a filter housing having an inlet and a dispensing outlet, b—a compressed gas cylinder, c—valve means for causing compressed gas to flow from said cylinder to said water container, d—first valve and first conduit means for causing water to flow from said container to said filter housing inlet;

e—a reservoir;

f—second valve and second conduit means for connecting said reservoir to said water container for controlling the level of the water in said reservoir;

g—third valve and third conduit means for connecting said reservoir to said filter housing inlet;

h—pressure gauge or transducer for monitoring the pressure at the filter housing inlet; and i—valve control means for causing said second and third valve and conduit means to connect said reservoir to said container and/or to said filter housing inlet or disconnect said reservoir from said container and/or said filter housing inlet.

* * * * *

UNITED STATES PATENT AND TRADEMARK OFFICE
CERTIFICATE OF CORRECTION

PATENT NO. : 6,527,146 B1
DATED : March 4, 2003
INVENTOR(S) : Tanny et al.

It is certified that error appears in the above-identified patent and that said Letters Patent is hereby corrected as shown below:

Column 1,
Line 15, "in the art The" should read -- in the art. The --
Lines 16-17, "*cryptorsproridium Parvum and giaria Lablia,*" should read -- *Cryptosproridium parvum and Giaria lamblia,* --
Line 26, "*pseudomonas Aurigena,*" should read -- *Pseudomonas aeruginosa,* --
Line 34, "unit sold Thus," should read -- unit sold. Thus, --
Line 35, "claimed retention In" should read -- claimed retention. In --

Column 3,
Line 20, "filter housing inlet" should read -- filter housing inlet. --
Line 60, "0.2 bar , and" should read -- 0.2 bar, and --

Column 4,
Line 10, "fictional" should read -- functional --
Line 20, "inlet The" should read -- inlet. The --
Line 33, "to it It also" should read -- to it. It also --
Line 49, "a reservoir," should read -- a reservoir; --
Line 53, "of the filter," should read -- of the filter; --

Column 5,
Line 25, "The filter be of any used" should read -- The filter can be of any type used --

Column 6,
Line 44, "sufficient t assure" should read -- sufficient to assure --

Column 7,
Line 12, "tat the filter" should read -- that the filter --

Column 8,
Line 19, "illustration It is" should read -- illustration. It is --
Line 50, "staring/stopping" should read -- starting/stopping --

UNITED STATES PATENT AND TRADEMARK OFFICE
CERTIFICATE OF CORRECTION

PATENT NO.    : 6,527,146 B1
DATED         : March 4, 2003
INVENTOR(S)   : Tanny et al.

It is certified that error appears in the above-identified patent and that said Letters Patent is hereby corrected as shown below:

Column 10,
Lines 34-35, "*cryptosporidium Parvum, giardia Lablia* and *pseudomonas Aurigena*" should read -- *Cryptosporidium parvum, Giardia lamblia,* and *Pseudomonas aeruginosa* --

Column 11,
Lines 44-45, "and first valve and first valve and conduit" should read -- and first valve and conduit --

Signed and Sealed this

Ninth Day of November, 2004

JON W. DUDAS
*Director of the United States Patent and Trademark Office*

UNITED STATES PATENT AND TRADEMARK OFFICE
CERTIFICATE OF CORRECTION

PATENT NO. : 6,527,146 B1
DATED : March 4, 2003
INVENTOR(S) : Tanny et al.

It is certified that error appears in the above-identified patent and that said Letters Patent is hereby corrected as shown below:

Title page,
Item [56], References Cited, FOREIGN PATENT DOCUMENTS, "EP 0 585 822 B1 2/1994" should read -- EP 0 582 822 B1  2/1994 --

Signed and Sealed this

Twenty-second Day of February, 2005

JON W. DUDAS
*Director of the United States Patent and Trademark Office*